(12) United States Patent
Kohli et al.

(10) Patent No.: US 8,835,509 B2
(45) Date of Patent: Sep. 16, 2014

(54) SELF EMULSIFYING DRUG DELIVERY SYSTEM FOR A CURCUMINOID BASED COMPOSITION

(75) Inventors: Kanchan Kohli, New Delhi (IN); Sunny Chopra, Chandigarh (IN); Saurabh Arora, New Delhi (IN); Roop K. Khar, New Delhi (IN); Kolappa K. Pillai, New Delhi (IN)

(73) Assignees: Arbro Pharmaceuticals Ltd., New Delhi (IN); Jamia Hamdard (Hamdard University), New Delhi (IN)

( * ) Notice: Subject to any disclaimer, the term of this patent is extended or adjusted under 35 U.S.C. 154(b) by 181 days.

(21) Appl. No.: 13/094,457

(22) Filed: Apr. 26, 2011

(65) Prior Publication Data

US 2011/0294900 A1  Dec. 1, 2011

(30) Foreign Application Priority Data

May 31, 2010   (IN) .......................... 1249/DEL/2010

(51) Int. Cl.
| | | |
|---|---|---|
| *A61K 31/12* | (2006.01) | |
| *A61K 9/66* | (2006.01) | |
| *A61K 47/34* | (2006.01) | |
| *A61K 47/44* | (2006.01) | |

(52) U.S. Cl.
CPC ................. *A61K 31/12* (2013.01); *A61K 47/34* (2013.01); *A61K 47/44* (2013.01)
USPC .......................................... 514/679; 424/455

(58) Field of Classification Search
USPC .......................................... 514/679; 424/455
See application file for complete search history.

(56) References Cited

U.S. PATENT DOCUMENTS

| | | | |
|---|---|---|---|
| 5,965,160 A | 10/1999 | Benita et al. | |
| 5,993,858 A | 11/1999 | Crison et al. | |
| 6,054,136 A | 4/2000 | Farah et al. | |
| 6,057,289 A | 5/2000 | Mulye | |
| 6,140,375 A | 10/2000 | Nagahama et al. | |
| 2007/0243132 A1* | 10/2007 | Russell-Jones et al. | 424/1.11 |

FOREIGN PATENT DOCUMENTS

| | | | |
|---|---|---|---|
| CN | 1895239 A | * | 1/2007 |
| WO | 2008/154705 A1 | | 12/2008 |
| WO | 2010/010431 A1 | | 1/2010 |

OTHER PUBLICATIONS

CN1895239 (A) Jianming et al. Curcumin preparation and its making method (Jan. 17, 2007), English translation.*

* cited by examiner

*Primary Examiner* — Jennifer M Kim
(74) *Attorney, Agent, or Firm* — Pergament Gilman & Cepeda LLP; Milagros A. Cepeda; Edward D. Pergament

(57) ABSTRACT

The present invention discloses a pharmaceutical composition in the form of self nano emulsifying drug delivery formulation comprising curcuminoids. The pharmaceutical composition of the present invention shows an enhanced drug loading ability, better stability and an improved bioavailability. The composition of the present invention comprises of a pharmaceutically effective amount of a curcuminoid, an oil phase, a surfactant and a co surfactant.

5 Claims, 1 Drawing Sheet

SELF EMULSIFYING DRUG DELIVERY SYSTEM FOR A CURCUMINOID BASED COMPOSITION

FIELD OF INVENTION

The present invention relates to a pharmaceutical composition comprising curcuminoid as a self emulsifying drug delivery formulation and the method of preparation thereof. The pharmaceutical composition of the present invention shows an enhanced drug loading ability, better stability and an improved bioavailability.

BACKGROUND OF THE INVENTION

Poor bioavailability of drugs has been a major limitation in the successful utilization of many therapeutic effective molecules. As it happens, most of these molecules are lipophilic in nature and tend to be poorly absorbed in the aqueous medium present in the Gastrointestinal (GI) tract. The problem of poor bioavailability is at times further compounded by a faster elimination rate which further reduces the efficiency of such molecules being used as a drug target of choice.

Curcuminoids, which are naturally occurring component in the common food spice turmeric (*Curcuma longa*), have been known to demonstrate wide range of therapeutic effects such as anti-inflammatory, anti-oxidant, anti-proliferative and anti-angiogenic. Curcumin is the principal curcuminoid present in turmeric. Chemically, curcumin is bis-$\alpha,\beta$-unsaturated $\beta$ diketone (commonly called diferuloylmethane, Formula 1). The other curcuminoids present in turmeric are, mainly, Bisdemethoxy curcumin and Demethoxy curcumin. In many cases, curcuminoid can be present solely or in combination with other active ingredients.

Formula 1

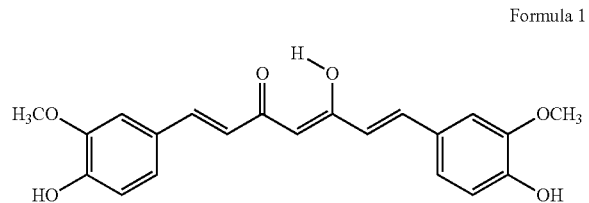 [SMILES: COc1cc(/C=C/C(=O)/C=C(O)/C=C/c2ccc(O)c(OC)c2)ccc1O]

In addition to its application in a wide spectrum of therapeutic areas, curcuminoids are also found to be safe even in high doses. These features make curcuminoids a potential target for developing therapies across multiple disease segments. Curcuminoids, however, suffer from a major disadvantage which acts as a blockade in its wider acceptance as a drug moiety of choice. It is found that curcuminoids has a reduced bioavailability within the body. This has been attributed to the lipophilic nature of curcuminoids and hence its poor absorption in the GI tract, rapid metabolism and quick elimination from the body. It was found, for example, by Rabindranath et al, (Absorption and tissue distribution of curcumins in rat. Toxicology, 1980 16(3), 259-265) that after oral administration of 400 mg of curcumins to rats, no curcumin was found in heart blood whereas a trace amount was found in the portal blood from 15 minute to 24 hour after the administration of curcumin.

Oral administration is regarded as the preferred route of drug intake offering numerous advantages including convenience, ease of compliance, potential for availability to large patent population and cost effectiveness. Thus oral bioavailability is a key factor in lead selection and development of new drugs. Poor oral bioavailability affects the drugs performance and leads to inter and intra patient variability. A number of chemotherapeutic as well as chemopreventive agents suffer from poor oral bioavailability rendering them unsuitable for oral delivery. Oral bioavailability depends primarily on—Drug permeability, Aqueous solubility, Dissolution rate, Presystemic metabolism, First-pass metabolism and Susceptibility to efflux mechanisms. Of these low permeability and poor solubility are the most common causes of poor oral bioavailability.

The advances in understanding the cause of poor bioavailability have led to significant improvements in the design of technologies to combat these deficiencies. The strategies to improve oral bioavailability can be grouped into three main groups comprising: Pro-drugs and drug conjugates, Medicinal chemistry and Formulation design. The present invention proposes the application of formulation design to enhance the oral bioavailability of selected drug candidate.

Formulation Design is often the route of choice for modifying the oral bioavailability of drugs as it offers a low cost and rapid solution to these problems particularly for drug already in the market. As opposed to pro-drug and medicinal chemistry approaches, Formulation Design does not require chemical modification of the drug or creation of New Chemical Entities. This provides considerable advantage in terms of reduced cost and development timeline. Poor aqueous solubility and dissolution rate frequently affect the oral performance of drugs. This issue has been successfully addressed in the art by using techniques such as, Co solvents, Micronization, Solid dispersions, Surfactants, Nano-Suspensions, Micro emulsions and Self Emulsifying Drug Delivery Systems (SEDDS).

Pre-formed Emulsions/Phospholipid complexes containing the lipophilic entity have been a tried and tested method to achieve a better solubility and absorption. This generally involves forming 'Lipids micelles' of the lipophilic entity with the help of suitable surfactant(s). Such micelles are then delivered as such at the absorption site. US Patent Publication US 20090324703 discloses one such curcuminoid-lipid micelles, wherein and the composition is provided as a microemulsion or solid lipid nanoparticles (SLN). Such microemulsion or SLN, no doubt, improved the absorption rate of the lipophilic moieties at the absorption site but nevertheless were only marginally better. A study by Suresh et al, (Studies on the in vitro absorption of spice principles-curcumin, capsaicin and piperin in rat intestine. Food Chem. Toxicol. 2007, 45 (8), 1437-42) showed that the absorption of curcumin when present as micelles increased was 56% as compared to 47% when present in a free form.

The advent of the Self Emulsifying Drug Delivery Systems (SEDDS) technique witnesses a marked improvement in the bioavailability of the lipophilic moieties. SEDDS comprise of an isotropic mixture of drug, oil, surfactant and/or co-solvents which upon oral administration gets emulsified in the aqueous media in the GI tract. The distinguishing feature of SEDDS is its ability to emulsify spontaneously to produce fine oil-in-water emulsions when introduced into an aqueous phase under gentle agitation. The resulting oil-in-water emulsion is thermodynamically stable due to the relatively small volume of the dispersed oil phase, the narrow range of droplet size distribution and the polarity of the oil droplets (Groves M J, Degalindez D A, The self-emulsifying action of mixed surfactants in oil, Acta Pharm Suec, 13, 1976, 361-372). The oil-in-water emulsion shows higher absorption in the GI tract. This approach has found a general acceptance for the lipophilic drugs that suffer from poor absorption rates. The SEDDS approach is being successfully followed in commercially available formulations containing cyclosporin A, ritonavir and squinavir.

The success of the self emulsifying technique in increasing the bioavailability of the drug depends on the oil-surfactant pair, surfactant concentration and the temperature at which self emulsification occurs. It is also widely understood that the droplet size also plays a key role in determining the absorption rate and hence the overall bioavailability of the drug molecule, as a small droplet size provides a large interfacial area for its absorption.

With the recent developments in nanotechnology, oil droplets of nano dimensions have been achieved. These nano sized oil droplets are more effective in increasing the bioavailability of the drug molecule, courtesy their size. These drug delivery systems are called Self Nano Emulsifying Drug Delivery System (SNEEDS). SEDDS now represent a broad category typically encompassing emulsions with a droplet size ranging between a few nanometers to several microns, while SNEDDS is used specifically where oil droplets are below 150 nm in size.

WO2008154705 discloses a curcumin based pre formed nanoemulsion for targeted delivery of a nano-shell containing the active ingredient. The '705 published application, however, does not contemplate any use of a self emulsifying drug delivery system.

WO2010010431 discloses a self nano emulsifying curcuminoid formulation. The '431 publication discloses use of surfactants that invariably cause the active ingredient, curcuminoid, to precipitate out of the aqueous medium even after half an hour of formation of the self emulsifying formulation. To combat this, the '431 publication further teaches the use of a polymeric molecular aggregation inhibitor, specifically Hydroxypropyl methyl cellulose (HPMC), in the formulation. As is widely known in the art, adding HPMC has its own disadvantages, prominent being the tendency of undissolved HPMC in an aqueous medium to form lumps. The undissolved HPMC is present in the medium even after protracted periods of agitation, thus the problem of lump formation poses a serious risk to the stability of the formulation. The formulation of '431 publication, thus, suffers from an inherent disadvantage of their choice of surfactant and then adding an extra additive to address that disadvantage.

It is, therefore, a need in the art to develop a self emulsifying curcuminoid composition which has an enhanced drug loading ability as well as an increased bioavailability and better stability. Further, a self emulsifying curcuminoid composition of such nature must also be able to address the lacunas present in the existing art, specifically as elaborated in the preceding paragraphs. Further, it would be desirable that such a composition is based on creating a nano emulsion at the absorption site so as to markedly increase the absorption efficiency.

OBJECT OF THE INVENTION

It is an object of the invention to provide a drug delivery system for a curcuminoid based pharmaceutical composition.

It is an object of the invention to provide a stable drug delivery system for a curcuminoid based pharmaceutical composition which results in an increased bioavailability of curcuminoid.

It is an object of the invention to provide a drug delivery system for a curcuminoid based pharmaceutical composition that spontaneously forms a nano-emulsion after coming in contact with the gastric fluid.

It is yet another object of the invention to provide a drug delivery system for a curcuminoid based pharmaceutical composition that has a curcuminoid loading capability more than 3%.

It is an object of the invention to provide a drug delivery system for a curcuminoid based pharmaceutical composition that does not require the use of a polymeric molecular aggregation inhibitor to maintain the stability of the composition.

It is an object of the invention to provide a drug delivery system for a curcuminoid based pharmaceutical composition that uses a surfactant which does not cause the curcuminoid to precipitate out of the aqueous medium once the nano emulsion is formed.

SUMMARY OF THE INVENTION

The present invention discloses a pharmaceutical composition in the form of self nano emulsifying drug delivery formulation comprising curcuminoids. The pharmaceutical composition of the present invention shows an enhanced drug loading capability, better stability and an improved bioavailability. The composition of the present invention comprises of a pharmaceutically effective amount of a curcuminoid, an oil phase, a surfactant and a co surfactant.

DETAILED DESCRIPTION OF THE INVENTION

Figure 1:
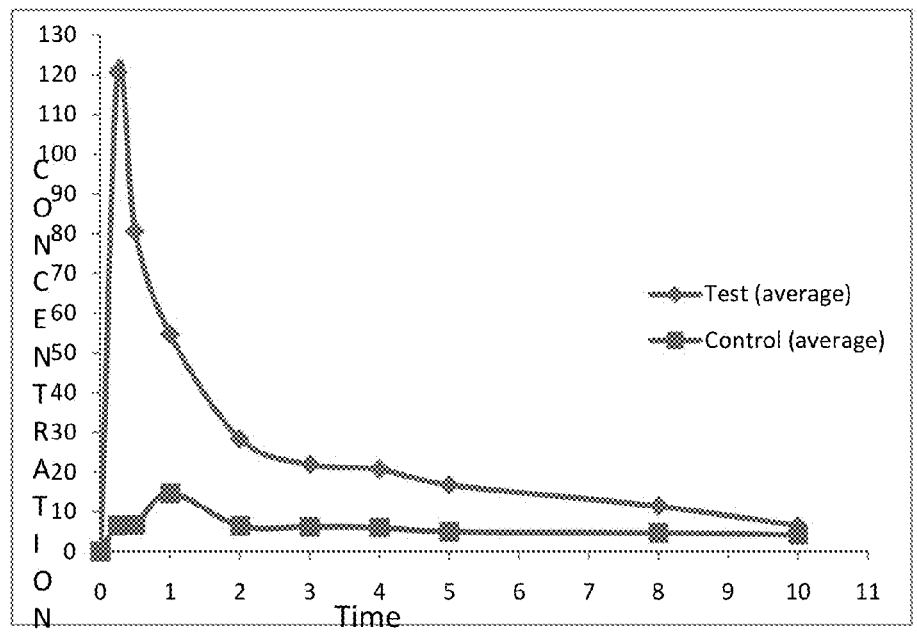
FIG. 1 illustrates the plasma concentration-time profiles obtained after oral administration of the self nano emulsifying formulation of Example 1 (blue) of the present invention with the aqueous suspension (Suspension A, Control). Concentration in ng/mL

The present invention describes a pharmaceutical composition comprising curcuminoids as a self nano emulsifying drug delivery formulation with an enhanced drug loading capability, better stability and an improved bioavailability.

In an embodiment, the pharmaceutical composition of the present invention comprises of a pharmaceutically effective amount of the curcuminoid, an oil phase, a surfactant and a co-surfactant In another embodiment of the present invention, the amount of curcuminoid is about 1% to 10% (w/w), preferably between 4% and 8% (w/w), most preferably between 5% to 6% (w/w) of the composition.

In an embodiment, the pharmaceutical composition of the present invention comprises of:
5-6% (w/w) of the curcuminoid;
25-33% (w/w) of the oil phase;
35-45% (w/w) of the surfactant, and
8-16% (w/w) of the co surfactant, In a preferred embodiment, the curcuminoid is curcumin.

In an embodiment, the oil phase of the composition of the present invention can be selected from a group comprising, propylene glycol esters, medium chain mono-, di-, or triglycerides, long chain fatty acids, edible oils, or a mixture thereof. In a preferred embodiment, the oil phase is selected from commercially available oils including, but not limited to, CAPTEX® 100 (Propylene Glycol Dicaprate), CAPTEX® 300 (Glyceryl Tricaprylate/Tricaprate), CAPTEX® 355 (Glyceryl Tricaprylate/Tricaprate), MIGLYOL® 810 (Caprylic/Capric Triglyceride), MIGLYOL® 812 (Caprylic/Capric Triglyceride), MIGLYOL® 818 (Caprylic/Capric/Linoleic Triglyceride), MIGLYOL® 829 (Caprylic/Capric/

Succinic Triglyceride), and DYNACERIN® 660 (Oleyl Erucate), CAPRYOL™ 90, CAPTEX® 200 (Propylene Glycol Dicaprylocaprate) and MIGLYOL® 840 (Propylene Glycol Dicaprylate/Dicaprate), and the like. In another embodiment, the oil phase is selected from a group comprising edible oils. In a preferred embodiment the edible oil is selected from a group comprising soyabean oil, castor oil, cottonseed oil, Arachis oil, sesame oil, sweet orange oil, canola oil, sunflower seed oil, peanut oil, rapeseed oil, and oleic acid. The active medicament generally has greater solubility in commercially available oil phases, and therefore, they are preferred over edible oils. In a most preferred embodiment, the oil phase is propylene glycol monocaprylate, commercially available as CAPRYOL™ 90. In an embodiment, the oil phase also acts as a co surfactant in the composition. The Hydrophilic-Lipophilic Balance (HLB) of the oil phase is between 2 and 10, more preferably between 4 and 8. The HLB value provides a means for ranking surfactants based on the balance between the hydrophilic and lipophilic portions of the surfactant or emulsifying agent. The higher the HLB number, the more hydrophilic the surfactant or emulsifying agent.

In an embodiment, the surfactants of the composition of the present invention are selected from ionic or non ionic surfactants.

In a preferred embodiment, the surfactants used in the present invention comprise non-ionic surfactants. In yet another embodiment, the non-ionic surfactants are selected from a group comprising polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives or a combination thereof. These are commercially available as CREMOPHOR® (From BASF) such as CREMOPHOR® EL (PEG-35 castor oil), CREMOPHOR® RH40 (PEG-40 hydrogenated castor oil), CREMOPHOR® RH60 (PEG-60 hydrogenated castor oil), LABRASOL® (PEG-8 Caprylic/Capric Glycerides), GELUCIRE® (Stearoyl polyoxylglycerides), Polysorbates, PLURONIC® L-64 and L-127 (block copolymers based on ethylene oxide and propylene oxide), TRITON™ X 100 (Polyethylene glycol tert-octylphenyl ether), SIMULSOL™ (polyoxyethylated products comprising Polyoxyethylated lauric alcohol, Polyoxyethylated cetostearyl alcohol, Polyoxyethylated stearic acid and the like) NIKKOL™ HCO-50 (Polyoxyethylene (50) hydrogenated castor oil), NIKKOL™ HCO-35 (Polyoxyethylene (35) hydrogenated castor oil), NIKKOL™ HCO-40 (Polyoxyethylene (40) hydrogenated castor oil), NIKKOL™ HCO-60 (Polyoxyethylene (60) hydrogenated castor oil) (From Nikko Chemicals Co. Ltd.), and TWEENS® (Polysorbates) (From ICI Chemicals). In a preferred embodiment, the surfactant is CREMOPHOR® EL. In yet another embodiment, the surfactant has a HLB between 9 and 18 and more preferably between 11 and 16.

The surfactant is capable of forming a stable emulsion, preferably a fine emulsion and more preferably a nanoemulsion, of the present composition when it is brought into contact with aqueous fluid, such as in the G.I. tract. The surfactant of the present invention does not precipitate out the active ingredient curcuminoid from the emulsion, and hence offers better stability of the formulation than the existing art. It also does away with the use of polymeric molecular aggregation inhibitors, as used in the existing art, to avoid the formation of curcuminoid precipitation.

In an embodiment, the co-surfactants of the present invention is selected from a group comprising polyethylene glycol chain lengths (preferably having a molecular weight of 200 to 600), propylene glycol derivatives, and commercially available products like TRANSCUTOL® (diethylene glycol monoethyl ether), CAPRYOL™ (Propylene glycol monocaprylate-Type I), CAPRYOL™ 90 (propylene glycol monocaprylate-Type II), CAPMUL® (glyceryl caprylate), TETRAGLYCOL™ (tetrahydrofurfuryl diethylene glycol ether), LABRAFIL® (Polyglycosyl glycerides), LUTROL® F68 (polaxomer 188), CARBITOL™ (diethylene glycol monoethyl ether) and the like. In a preferred embodiment, the co-surfactant is polyethylene glycol (PEG) with molecular weight of 200, commonly known as PEG-200. In an embodiment, the co-surfactants of the present invention also act as solubilizers in the resulting composition.

In an embodiment, the composition of the present invention can comprise additives conventionally used for preparing pharmaceutical formulations. These can include pH buffers, gelling agents, and stabilizing components. In an embodiment, the pH buffer is selected from a group comprising acetic acid, glacial acetic acid, lactic acid, citric acid, phosphoric acid, carbonic acid, histidine, glycine, barbital, phthalic acid, adipic acid, ascorbic acid, maleic acid, succinic acid, tartaric acid, glutamic acid, benzoic acid, aspartic acid, and salts (e.g., potassium, sodium, etc.) or combinations thereof.

In an embodiment, the gelling agent is selected from a group comprising of xanthan gum, carrageenan, locust bean gum, guar gum, modified celluloses, low-esterified pectines, and colloidal silicon dioxide. In a preferred embodiment, the gelling agent is colloidal silicon dioxide, commercially available as Aerosil.

In an embodiment, the stabilizing component of the formulation is selected from a group comprising of α-tocopherol, ascorbyl palmitate, BHT (butyl hydroxytoluene), BHA (butyl hydroxyanisole), propyl gallate or malic acid.

The curcuminoid composition of the present invention forms an oil/water nanoemulsion instantaneously when brought into contact with the aqueous medium of the GI tract with mild agitation provided by gastric mobility in the tract region. The formation of nanoemulsion leads to a superior absorption and enhanced bioavailability of the curcuminoid enabling reduction in dose, more consistent temporal profiles of drug absorption, and protection of drugs from the hostile environment in gut.

In a preferred embodiment, the droplet size of the composition of the present invention is 60-150 nm. The composition of the present invention, by virtue of its choice of surfactants, does not lead to any precipitation of the active ingredient, and subsequently also does away with the use of any polymeric molecular aggression inhibitors, thus providing a composition that is effective and stable over a wide period of time. Further, a stable self nano emulsifying composition with a curcuminoid loading ability of around more than 3%, hitherto unachieved, is a marked advancement over the existing art and paves way for further research and development on curcuminoids as a better, safer and efficient drug of choice.

The curcuminoid composition of the present invention is ideal for oral delivery systems, since they are homogeneous, thermodynamically stable, have uniform droplet sizes, and are optically clear. The curcuminoid composition of the present invention can be administered in the form of liquid or solid dosage form. In an embodiment, when administered as a liquid dosage form, the composition is filled in hard or soft gelatin capsules.

Oral unit dosage forms in accordance with the present invention will suitably comprise from 5 to 400 mg and more preferably from 20 to 200 mg of the curcuminoid. The dosage of the drug and the number of times it is administered to the patient will vary depending on several factors including but not limited to the age of the patient, the severity of the condition of the patient, past medical history, among other factors, and will be determined by the physician in his sound discretion.

The composition of the present invention are preferably administered to mammals, such as dog, cat, horse, pig, mice, rat and especially humans. When the composition of the present invention is prepared in the form of a soft or hard capsule, the composition may be encapsulated in a gelatin shell which contains any conventional plasticizer. Preferably, the plasticizer is selected from a group consisting of glycerine, sorbitol, hexanetriol propylene carbonate, hexane glycol, sorbitans, tetrahydrofuryl alcohol ether, diethylene glycol monoethyl ether, 1,3-trimethyl-2-imidazolidone, and dimethylisosorbide The composition of the present invention can be adsorbed on silicates/microcrystalline cellulose and subsequently compressed into tablets.

The pharmaceutical compositions of the present invention were prepared by the following steps:
 a) Curcuminoid was added to CAPRYOL™ 90 to form a dispersion;
 b) CREMOPHOR® EL was added to the dispersion formed in Step (a);
 c) TRANSCUTOL® HP was added to the dispersion formed in Step (b)
 d) PEG 200 was added to the dispersion formed in Step (c)
 e) The dispersion obtained from Step (d) was ready for encapsulation and was filled in hard/soft gelatin capsules.

The present invention provides a drug delivery system for a curcuminoid based pharmaceutical composition.

The present invention provides a stable drug delivery system for a curcuminoid based pharmaceutical composition which results in an increased bioavailability and curcuminoid.

The present invention provides a drug delivery system for a curcuminoid based pharmaceutical composition that spontaneously forms a nano-emulsion after coming in contact with the gastric fluid.

The present invention provides a drug delivery system for a curcuminoid based pharmaceutical composition that has a curcuminoid loading capability of more than 3%.

The present invention provides a drug delivery system for a curcuminoid based pharmaceutical composition that does not require the use of a polymeric molecular aggregation inhibitor to maintain the stability of the composition.

The present invention provides a drug delivery system for a curcuminoid based pharmaceutical composition that uses a surfactant which does not cause the curcuminoid to precipitate out of the aqueous medium once the nano emulsion is formed.

EXAMPLES

The present invention is further explained in the form of following examples. However it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example 1

Self Nano Emulsifying Drug Delivery Formulation (SNEEDS)

| Component | Composition (in % w/w) |
|---|---|
| CREMOPHOR® EL | 40.98 |
| CAPRYOL™ 90 | 28.82 |
| TRANSCUTOL® HP | 11.03 |
| PEG 200 | 13.59 |
| Curcuminoid | 5.58 |

Procedure of Preparation:
 a) Curcuminoid was added to CAPRYOL™ 90 to form a dispersion;
 b) CREMOPHOR® EL was added to the dispersion formed in Step (a);
 c) TRANSCUTOL® HP was added to the dispersion formed in Step (b)
 d) PEG 200 was added to the dispersion formed in Step (c)
 e) The dispersion obtained from Step (d) was ready for encapsulation and was filled in hard gelatin capsules.

Example 2

Self Nano Emulsifying Drug Delivery Formulation

| Component | Composition (in % w/w) |
|---|---|
| CREMOPHOR® EL | 42.36 |
| CAPRYOL™ 90 | 30.35 |
| TRANSCUTOL® HP | 10.46 |
| PEG 200 | 13.59 |
| Curcuminoid | 3.24 |

Example 3

Self Nano Emulsifying Drug Delivery Formulation

| Component | Composition (in % w/w) |
|---|---|
| CREMOPHOR® EL | 46.32 |
| CAPRYOL™ 90 | 25.28 |
| TRANSCUTOL® HP | 11.03 |
| PEG 200 | 12.25 |
| Curcuminoid | 5.12 |

Example 4

Self Nano Emulsifying Drug Delivery Formulation

| Component | Composition (in % w/w) |
|---|---|
| CREMOPHOR® EL | 39.73 |
| CAPRYOL™ 90 | 24.90 |

-continued

| Component | Composition (in % w/w) |
|---|---|
| TRANSCUTOL® HP | 14.32 |
| PEG 200 | 14.84 |
| Curcuminoid | 6.21 |

Example 5

Self Nano Emulsifying Drug Delivery Formulation

| Component | Composition (in % w/w) |
|---|---|
| CREMOPHOR® EL | 38.71 |
| CAPRYOL™ 90 | 28.51 |
| TRANSCUTOL® HP | 11.03 |
| PEG 200 | 16.32 |
| Curcuminoid | 5.43 |

Procedure of preparation of Examples 2 to 5: Same procedure was followed in Example 2-5 as given for Example 1.

Example 6

Solubility Test

The solubility of curcumin in a number of oils such as citronella oil, castor oil, ethyl oleate, and palm rose oil, coconut oil, CAPRYOL™ 90 and a number of surfactants such as TWEEN® 80, CREMOPHOR® EL, PEG 200 and TRANSCUTOL® HP were determined in order to find out the appropriate oils and surfactants as compositions of SNEDDS. Solubility was also determined in milk, BSA and casein.

Figure 2:
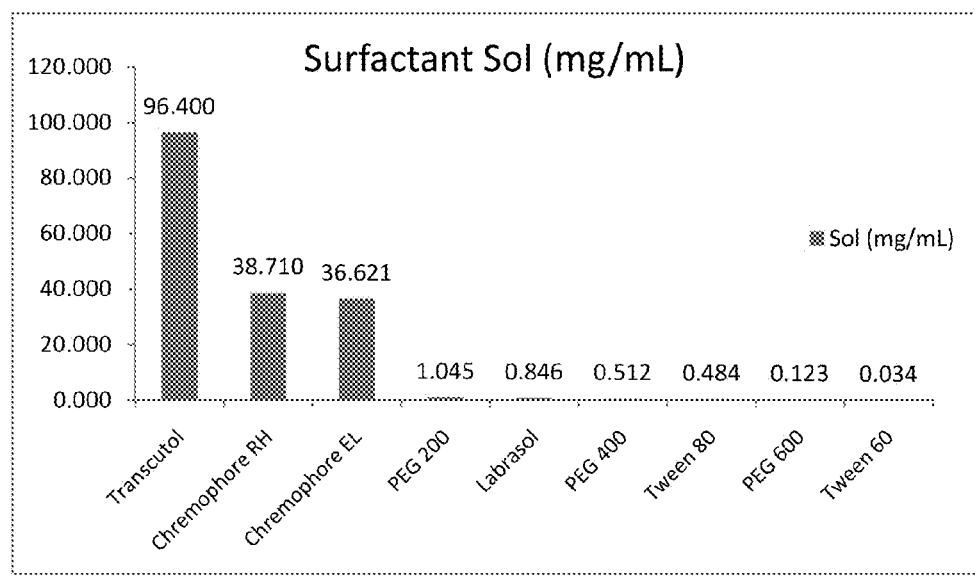
FIG. 2 illustrates the solubility of Curcumin in surfactants.

An excess amount of curcumin was added to 5 ml of oil or surfactant solutions. The resultant mixture was shaken reciprocally at 37° C. for 72 h, followed by centrifugation at 12000 rpm for 10 min. The supernatant was filtered through a membrane filter (0.45 µm) to remove the remaining insoluble curcumin. After the appropriate dilution with methanol, the drug concentration in the filtrate was quantified by HPLC. The results of the solubility test are provided in Table 1, 2 and 3 and FIG. 2.

TABLE 1

Solubility of Curcumin in oils

| Oil | Sol (mg/mL) |
|---|---|
| Citronella | 13.204 |
| CAPRYOL™ 90 | 7.575 |
| Palm Rose | 6.033 |
| Castor | 4.420 |
| Labrafilm F2125 | 3.593 |
| Lavender | 3.445 |
| Lauroglycol | 2.613 |
| Labrafilm F 1944 | 2.562 |
| Cocconut Oil | 1.683 |
| Emu oil | 1.585 |
| Almond | 1.250 |
| IPM | 1.128 |
| Ethyl Oleate | 0.589 |
| Oilve | 0.501 |
| Linseed Oil | 0.277 |
| *Arachis* Oil | 0.160 |
| Glyc Mono ol | 0.154 |
| Light Paraffin | 0.007 |

TABLE 2

Solubility of Curcumin in surfactants

| Surfactant (used in 100% conc) | Sol (mg/mL) |
|---|---|
| TRANSCUTOL® HP | 96.400 |
| CREMOPHOR® RH | 38.710 |
| CREMOPHOR® EL | 36.621 |
| PEG 200 | 1.045 |
| LABRASOL® | 0.846 |
| PEG 400 | 0.512 |
| TWEEN® 80 | 0.484 |
| PEG 600 | 0.123 |
| TWEEN® 60 | 0.034 |

TABLE 3

Solubility of Curcumin in milk, BSA and Casein

| | Solubility mg/mL |
|---|---|
| Milk | 23.776 |
| BSA | 0.024 |
| Casein | 0.014 |

Example 7

In Vivo Activity of Self-Emulsifying Self Nano Emulsifying Drug Delivery Formulation Tests were carried out to compare bioavailability of curcumin after oral administration of the self nano emulsifying formulation of Example 1 of the present invention with the aqueous suspension (Suspension A).

Twenty animals were fasted overnight. Ten animals (5 Males and 5 Females) were administered orally Y mL Formulation A using rat feeding tube which was subsequently followed by feeding them 1 mL of water using rat feeding tube and ten animals (5 Males and 5 Females) were administered Z mL Suspension A of Curcumin. Dose selected in both test and control rats was 180 mg/kg body weight. Blood samples (0.5 mL) were withdrawn from the retro orbital plexus of rats at following time points 0, 0.25, 0.5, 1, 2 h, 3 h, 4 h, 6 h, 8 h and 10 h using heparinised rat bleeding capillary. Blank samples were taken in the same way in the beginning without administering rat with any drug and was coded BL Plasma was extracted (by centrifuging blood samples at 3000 rpm for 8 min) from blood Samples and suitably diluted which was subsequently analyzed on LC/MS

TABLE 4

Rats administered with Suspension of curcumin (CONTROL)

| S. No | Weight of Rats | Dose administered (Z mL) |
|---|---|---|
| 1. | 210 | 2.057 |
| 2. | 225 | 2.205 |
| 3. | 210 | 2.057 |
| 4. | 200 | 1.959 |
| 5. | 190 | 1.862 |
| 6. | 225 | 2.205 |
| 7. | 220 | 2.156 |
| 8. | 325 | 3.185 |
| 9. | 300 | 2.939 |
| 10. | 300 | 2.939 |

TABLE 5

Rats administered with Self Nano emulsifying Formulation of curcumin of Example 1

| S. No | Weight of Rats | Dose administered (Y mL) |
|---|---|---|
| 1. | 190 | 0.775 |
| 2. | 220 | 0.898 |
| 3. | 220 | 0.898 |
| 4. | 300 | 1.224 |
| 5. | 275 | 1.122 |
| 6. | 310 | 1.265 |
| 7. | 210 | 0.857 |
| 8. | 210 | 0.857 |
| 9. | 205 | 0.837 |
| 10. | 225 | 0.918 |

The results show that the plasma concentration obtained for the self nonoemulsifying formulation were significantly higher than the aqueous suspension and are maintained for a longer time thus increasing the biological half life of the drug. The results are summarized in Table 3 and FIG. 1.

TABLE 6

Comparison of plasma concentration (ng/mL) of curcumin in control rats (following oral administration of curcuminoid suspension) and test rats (following oral administration of curcuminoid formulation)

| Time (hrs) | Control (average) ng/mL | Standard Deviation | Test (average) ng/mL | Standard Deviation |
|---|---|---|---|---|
| 0 | 0 | 0 | 0 | 0 |
| 0.25 | 6.62 | 2.836 | 120.825 | 20.4479 |
| 0.5 | 6.71 | 2.841 | 80.65 | 17.725 |
| 1 | 14.63 | 4.867 | 54.675 | 12.982 |
| 2 | 6.45 | 3.149 | 28.3875 | 8.684 |
| 3 | 6.20 | 3.12 | 21.8875 | 6.438 |
| 4 | 5.99 | 2.97 | 20.7125 | 5.86 |
| 5 | 4.96 | 2.532 | 16.7375 | 5.1 |
| 8 | 4.67 | 2.178 | 11.34875 | 4.653 |
| 10 | 4.17 | 2.119 | 6.49 | 3.231 |

TABLE 7

Comparison of pharmacokinetic parameters obtained after oral administration of the self nano emulsifying formulation of Example 1 of the present invention with the aqueous suspension of curcuminoid (Suspension A, Control)

| Treatment | Kel (1/hr) | Tmax (hr) | Cmax (ng/ml) | AUClast (hr * ng/ml) | AUMClast (hr * hr * ng/ml) |
|---|---|---|---|---|---|
| Control | 0.0553 | 1 | 14.63 | 59.5488 | 252.8 |
| Test | 0.1717 | 0.25 | 120.825 | 240.7806 | 728.22 |

Example 8

Stability Study of the Self Nano Emulsifying Formulation of the Present Invention of Example 1

Example 1 formulation was packed in blister pack or glass bottle and stability data was generated.

Stability studies were carried out for the Formulation at 40° C./75% Relative Humidity for six months.

The formulation was found to be stable for at least 6 months at accelerated stability conditions in both the packs. The results of the stability study are provided in Table 5.

TABLE 8

Stability studies data of curcuminoid SNEDDS of Example 1 in blister pack and glass bottle

| Time | Blister pack (Assay) | Glass bottle (Assay) |
|---|---|---|
| 0 Month | 99.1% | 99.1% |
| 1 Month | 96.9% | 97.3% |
| 2 Month | 96.4% | 96.5% |
| 3 Month | 95.1% | 95.6% |
| 6 Month | 93.0% | 94.1% |

Example 9

Dispersibility Study

Dispersibility study was performed to evaluate the efficiency of dispersibility of oral nanoemulsion. 2 mL of each formulation of Example 1 to Example 5 was added to 500 mL of distilled water and 0.1N HCl in a standard USP XXII dissolution apparatus 2. Speed of the paddle was adjusted to 50 rpm and the temperature was maintained at 37±0.5° C. (Pouton C W, 1997). The formulations were visually evaluated for clarity. The results are summarized in Table 9.

Example 10

Particle Size Distribution

One gram of each of the Formulations of Example 1 to 5 was diluted in 200 ml-0.1N HCl. The droplet size/distribution of the prepared solution was determined using MALVERN Particle Size Analyzer (Model Zetasizer Ver. 6.01, Malvern Instruments, UK). using He—Ne Red laser, 4.0 mW, 632.9 nm; temperature, 25° C.; refractive index, 1438; or with adjustment if needed. Each sample was analyzed in triplicate.

It was found that Example 1 formulation had 90% of the particles having particle size less than 90 nm.

The average Particle size was determined to be 90 nm with 95.6% particles having particle size of 85 nm

Example 11

Solubilty Study

The solubility of Curcuminoid is determined in each of the Formulations of Example 1 to 5 using the method as described in Example 6. The results are summarized in Table 9.

TABLE 9

| Formulation of | Particle size (nm) | Curcuminoid Solubility | Dispersability Water | 0.1N HCl |
|---|---|---|---|---|
| Example 1 | 90 nm | 60 mg/mL | Clear | Clear |
| Example 2 | 85 nm | 35 mg/mL | Clear | Clear |
| Example 3 | 130 nm | 50 mg/mL | Clear | Hazzy |
| Example 4 | 200 nm | 70 mg/mL | Hazzy | Clear |
| Example 5 | 160 nm | 55 mg/mL | Clear | Hazzy |

Example 12

In-Vitro Dissolution Study

The dissolution behaviors of curcumin-loaded SNEDDS were compared with pH 1.2, pH 6.8 and ph 4.5 buffer solutions. SNEDDS containing 60 mg of curcumin was filled in hard gelatin capsules and introduced into 500 ml of a dissolution medium and maintained at 37° C. in USP II dissolution apparatus using Japanese sinkers. The revolution speed of the paddle was kept constant at 100 rpm. The aliquot of 5 ml was withdrawn at 0, 10, 20, 30, 50 and 60 min, and filtered through 0.45 µm membrane filters. The concentration of curcumin was determined spectrophotometrically at 423 nm. The removed volume was replaced each time with 5 ml of fresh medium. The dissolution of each capsule is calculated and the results are shown in Table 10.

TABLE 10

Results of the Dissolution Study

| Time (min) | % drug released | | |
|---|---|---|---|
| | 0.1N HCl | 4.5 Acetate buffer | 6.8 Phosphate buffer |
| 0 | 0 | 0 | 0 |
| 10 | 83.5 | 83 | 82 |
| 20 | 96.8 | 96.4 | 95.7 |
| 30 | 99.5 | 99.2 | 98.6 |
| 45 | 99.7 | 99.5 | 99.3 |
| 60 | 100 | 100 | 100 |

We claim:

1. A self-emulsifying drug delivery system for a pharmaceutical composition, said system comprising,
   a pharmaceutically effective amount of curcuminoid present in a range of 1-10% (w/w);
   an oil phase wherein said oil phase is propylene glycol monocaprylate present in a range of 25-33% (w/w);
   a surfactant, wherein said surfactant is a polyoxyethylene or polyethoxyl derivative of a vegetable oil present in a range of 35-45% (w/w);
   one or more co-surfactant(s) present in a range of 8-16% (w/w), wherein said co surfactant(s) is/are different from said surfactant;
   further wherein said composition is substantially free of polymeric molecular aggregation inhibitor;
   further wherein said pharmaceutical composition spontaneously forms a nano emulsion when brought in contact with an aqueous fluid of human gastrointestinal tract;
   further wherein said composition at 40° C./75 relative humidity is stable for at least 6 months;
   further wherein said composition has drug loading capability of more than 3%; and
   further wherein said composition has at least 8 fold increase in Cmax and at least 4 fold increase in AUC as compared to curcuminoid aqueous suspension.

2. The system as claimed in claim 1, wherein said curcuminoid is Curcumin.

3. The system as claimed in claim 1, wherein said surfactant is a non-ionic surfactant and selected from a group consisting of polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives or a combination thereof.

4. The system as claimed in claim 1, wherein said co-surfactant is selected from a group consisting of polyethylene glycol, diethylene glycol monoethyl ether, glyceryl caprylate, tetrahydrofurfuryl diethylene glycol ether, polyglycosyl glycerides, polaxomer 188 and diethylene glycol monoethyl ether.

5. The system as claimed in claim 1, wherein said pharmaceutical composition is in an oral dosage form and further comprises of pharmaceutically acceptable additives selected from a group comprising of pH buffers, gelling agents, and stabilizing components and their combinations thereof.

* * * * *